United States Patent
Olah et al.

(10) Patent No.: US 7,906,559 B2
(45) Date of Patent: Mar. 15, 2011

(54) CONVERSION OF CARBON DIOXIDE TO METHANOL AND/OR DIMETHYL ETHER USING BI-REFORMING OF METHANE OR NATURAL GAS

(75) Inventors: George A. Olah, Beverly Hills, CA (US); G. K. Surya Prakash, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 568 days.

(21) Appl. No.: 11/850,501

(22) Filed: Sep. 5, 2007

(65) Prior Publication Data

US 2008/0319093 A1    Dec. 25, 2008

Related U.S. Application Data

(60) Provisional application No. 60/945,501, filed on Jun. 21, 2007.

(51) Int. Cl.
*C07C 27/00*    (2006.01)
(52) U.S. Cl. .................................................... 518/704
(58) Field of Classification Search .................. None
See application file for complete search history.

(56) References Cited

U.S. PATENT DOCUMENTS

| 3,993,457 A | * | 11/1976 | Cahn et al. | 48/197 R |
| 4,093,029 A | | 6/1978 | Weisz et al. | 166/305 |
| 4,395,495 A | | 7/1983 | Cummings | 518/704 |
| 4,640,766 A | | 2/1987 | Post et al. | 208/111 |
| 5,599,638 A | | 2/1997 | Surampudi et al. | 429/33 |

FOREIGN PATENT DOCUMENTS

| EP | 0 159 759 B1 | 10/1985 |
| GB | 1 545 329 | 5/1979 |
| WO | WO 2006/113294 A1 | 10/2006 |
| WO | WO 2007/014487 A1 | 2/2007 |

OTHER PUBLICATIONS

International Search Reports for PCT/US2008/067462, Sep. 2008.
International Search Report and the Written Opinion of the International Searching Authority, application No. PCT/US2008/067480, dated Oct. 1, 2008.

* cited by examiner

*Primary Examiner* — Rosalynd Keys
(74) *Attorney, Agent, or Firm* — Winston & Strawn LLP

(57) ABSTRACT

The invention discloses a method of converting carbon dioxide to methanol and/or dimethyl ether using any methane source or natural gas consisting of a combination of steam and dry reforming, in a specific ratio to produce a 2:1 molar ratio of hydrogen and carbon monoxide with subsequent conversion of the CO and $H_2$ mixture exclusively to methanol and/or dimethyl ether. This method is termed the BI-REFORMING™ process. Dehydrating formed methanol allows producing dimethyl ether (DME) using any suitable catalytic method, including use of solid acid catalysts. When recycling formed water into the bi-reforming step the conversion of carbon dioxide with methane produces exclusively dimethyl ether without any by-product formation and complete utilization of hydrogen.

16 Claims, 2 Drawing Sheets

CONVERSION OF CARBON DIOXIDE TO METHANOL AND/OR DIMETHYL ETHER USING BI-REFORMING OF METHANE OR NATURAL GAS

This application claims the benefit of application No. 60/945,501 filed Jun. 21, 2007. The entire content of that application is expressly incorporated herein by reference thereto.

BACKGROUND

Hydrocarbons are essential in modern life. Hydrocarbons are used as fuel and raw material in various fields, including the chemical, petrochemical, plastics, and rubber industries. Fossil fuels, such as coal, oil and natural gas, are composed of hydrocarbons with varying ratios of carbon to hydrogen. Despite their wide application and high demand, fossil fuels also have limitations and disadvantages, particularly due to their finite reserve, irreversible combustion and contribution to air pollution (and thus to global warming). Regardless of these problems the more efficient use of still existing natural gas sources is highly desirable. Further new sources and ways for recyclable and environmentally benign carbon fuels are needed.

One alternative frequently mentioned non-carbon fuel is hydrogen, and its use in the so-called "hydrogen economy." Hydrogen is thought to be beneficial as a clean fuel, producing only water when combusted. Free hydrogen, however, is not a natural primary energy source on earth, due to its incompatibility with atmospheric oxygen. It must be generated from hydrocarbons or water is a highly energy-consuming process. Further, as hydrogen is produced from hydrocarbons or coal, any claimed benefit of hydrogen as a clean fuel is outweighed by the fact that its generation, mainly by reforming of natural gas, oil or coal to synthesis gas ("syn-gas" a mixture of CO and $H_2$), or the generation of electricity for the electrolysis of water is far from clean, besides hydrogen is difficult and costly to handle, transport and distribute. As it is extremely light, volatile and potentially explosive, it requires high-pressure equipment. The needed non-existent infrastructure also necessitates special materials to minimize diffusion and leakage, and extensive safety precautions to prevent explosions.

The continued importation of natural gas from far away and frequently difficult to access locations also necessitates its safe storage and transportation particularly when involving to LNG (liquefied natural gas). This necessities transporting LNG at low temperatures in its liquid form over the seas exposing it to serious environmental and safety hazards including terrorism. It is suggested that a more practical and safe alternative for LNG is methanol, or dimethyl ether (DME), which are readily produced from natural gas (vide infra). Methanol, $CH_3OH$, is the simplest liquid oxygenated hydrocarbon, differing from methane ($CH_4$) by a single additional oxygen atom. Methanol, also called methyl alcohol or wood alcohol, is a colorless, water-soluble liquid with a mild alcoholic odor. It is easy to store and transport. It freezes at −97.6° C., boils at 64.6° C., and has a density of 0.791 at 20° C.

Methanol is a convenient safe liquid easily obtained from existing coal or natural gas sources via methods developed and practiced since the 1920's. However, these methods using conversion (reforming) of coal and subsequently natural gas to syn-gas (a mixture of $H_2$ and CO) are highly energy consuming and produce large amount of $CO_2$ as a by-product. This is notably an economic disadvantage but also represents a serious environmental problem by increasing a main greenhouse gas (causing global warming).

Methanol not only represent a convenient and safe way to store and transport energy, but together with its derived product dimethyl ether (DME), is an excellent fuel. Dimethyl ether is easily obtained from methanol by dehydration or from methane (natural gas) with $CO_2$ via bi-reforming. It is a particularly effective fuel for diesel engines because of its high cetane number and favorable combustion properties. Methanol and dimethyl ether exceedingly blend well with gasoline or diesel oil to be used as fuels in internal combustion engines or electricity generators. One of the most efficient use of methanol is in fuel cells, particularly in direct methanol fuel cells (DMFC), in which methanol is directly oxidized with air to carbon dioxide and water while producing electricity.

Contrary to gasoline, which is a complex mixture of many different hydrocarbons and additives, methanol is a single simple chemical compound. It contains about half the energy density of gasoline, meaning that two liters of methanol provide the same energy as a liter of gasoline. Even though methanol's energy content is lower, it has a higher octane rating of 100 (average of the research octane number (RON) of 107 and motor octane number (MON) of 92), which means that the fuel/air mixture can be compressed to a smaller volume before being ignited. This allows the engine to run at a higher compression ratio of 10-11 to 1 more efficiently than the 8-9 to 1 ratio of a gasoline-powered engine. Efficiency is also increased by methanol's (and oxygenate) higher "flame speed," which enables faster, more complete fuel combustion in the engines. These factors explain the high efficiency of methanol despite its lower energy density than gasoline. Further, to render methanol more ignitable even under the most frigid conditions, methanol is mixed with gasoline, and other volatile components or with a device to vaporize or atomize methanol. For example, an effective automotive fuel comprised by adding methanol to gasoline with the fuel having a minimum gasoline content of at least 15% by volume (M85 fuel) so that it can readily start even in low temperature environments were commercially used in the US in the 1980's. M20 fuel (with 20 volume % methanol) is also being introduced. Similarly, dimethyl ether (DME) mixed with diesel oil or in household use as a substitute of natural gas or LPG is of commercial interest. These mixtures are not only efficient fuels but conserve or replace decreasing oil resources. The amount of methanol or dimethyl ether added can be determined depending upon the specific condition and needs.

Methanol has a latent heat of vaporization of about 3.7 times higher than gasoline, and can absorb a significantly larger amount of heat when passing from liquid to gaseous state. This helps remove heat away from the engine and enables the use of an air-cooled radiator instead of a heavier water-cooled system. Thus, compared to a gasoline-powered car, a methanol-powered engine provides a smaller, lighter engine block, reduced cooling requirements, and better acceleration and mileage capabilities. Methanol and DME are also more environment-friendly than gasoline or diesel oil, and produce low overall emissions of air pollutants such as certain hydrocarbons, $NO_x$, $SO_2$ and particulates.

Methanol is also one of the safest fuels available. Compared to gasoline, methanol's physical and chemical properties significantly reduce the risk of fire. Methanol has lower volatility, and methanol vapor must be four times more concentrated than gasoline for ignition to occur. Even when ignited, methanol burns about four times slower than gasoline, releases heat only at one-eighth the rate of gasoline fire, and is far less likely to spread to surrounding ignitable materials because of the low radiant heat output. It has been estimated by the EPA that switching from gasoline to methanol would reduce incidence of fuel-related fire by 90%. Methanol burns with a colorless flame, but additives can solve this problem. As methanol is completely miscible with water not only it is environmentally readily decomposed in nature but in contrast to ethanol there are no strict requirements needed to keep it dry to avoid phase separation from gasoline.

Methanol and/or DME also provide an attractive and more environmentally-friendly alternative to diesel fuel. They do not produce smoke, soot, or particulates when combusted, in contrast to diesel fuel, which generally produces polluting particles during combustion. They also produce very low emissions of NOx because they burn at a lower temperature than diesel. Furthermore, they have a significantly higher vapor pressure compared to diesel fuel, and the higher volatility allows easy start even in cold weather, without producing smoke typical of cold start with a conventional diesel engine. If desired, additives or ignition improvers, such as octyl nitrate, tetrahydrofurfuryl nitrate, peroxides or higher alkyl ethers, can be added to bring methanol's cetane rating to the level closer to diesel. Methanol is also used in the manufacture of biodiesel fuels by esterification of fatty acids.

As mentioned closely related and derived from methanol, and highly desirable alternative fuel is dimethyl ether. Dimethyl ether (DME, $CH_3OCH_3$), the simplest of all ethers, is a colorless, nontoxic, non-corrosive, non-carcinogenic and environmentally friendly chemical that is mainly used today as an aerosol propellant in spray cans, in place of the banned CFC gases. DME has a boiling point of −25° C., and is a gas under ambient conditions. DME is, however, easily handled as liquid and stored in pressurized tanks, much like liquefied petroleum gas (LPG). The interest in dimethyl ether as alternative fuel lies in its high cetane rating of 55 to 60, which is much higher than that of methanol and is also higher than the cetane rating of 40 to 55 of conventional diesel fuels. The cetane rating indicates that DME can be effectively used in diesel engines. Advantageously, DME, like methanol, is clean burning, and produces no soot particulates, black smoke or $SO_2$, and only very low amounts of $NO_x$ and other emissions even without after-treatment of its exhaust gas. Some of the physical and chemical properties DME, in comparison to diesel fuel, are shown in Table 1.

TABLE 1

Comparison of the physical properties of DME and diesel fuel

| | DME | Diesel fuel |
| --- | --- | --- |
| Boiling point ° C. | −24.9 | 180-360 |
| Vapor pressure at 20° C. (bar) | 5.1 | — |
| Liquid density at 20° C. (kg/m³) | 668 | 840-890 |
| Heating value (kcal/kg) | 6,880 | 10,150 |
| Cetane number | 55-60 | 40-55 |
| Autoignition temperature (° C.) | 235 | 200-300 |
| Flammability limits in air (vol %) | 3.4-17 | 0.6-6.5 |

Currently, DME is produced by direct dehydration of methanol.

$$2CH_3OH \rightarrow CH_3OCH_3 + H_2O$$

Another methanol derivative is dimethyl carbonate (DMC), which can be obtained by converting methanol with phosgene or by oxidative carbonylation of the methanol. DMC has a high cetane rating, and can be blended into diesel fuel in a concentration up to 10%, reducing fuel viscosity and improving emissions.

Methanol and its derivatives, e.g., DME, DMC, and biodiesel (esters of naturally occurring unsaturated acids) already have significant and expanding uses. They can be used, for example, as a substitute for gasoline and diesel fuel in ICE-powered cars with only minor modifications to the existing engines and fuel systems. Methanol can also be used in fuel cells, for fuel cell vehicles (FCVs), which are considered to be the best alternatives to ICEs in the transportation field. DME is also starting to be used in admixture to LNG and LPG in domestic and industrial fuel uses.

Methanol can also be used in reforming to produce hydrogen. In an effort to address the problems associated with hydrogen storage and distribution, suggestions have been made to use liquids rich in hydrogen such as gasoline or methanol as a source of hydrogen in vehicles via an on-board reformer. It was emphasized that methanol is the safest of all materials available for such hydrogen production. Further, because of the high hydrogen content of liquid methanol, even compared to pure cryogenic hydrogen (98.8 g of hydrogen in a liter of methanol at room temperature compared to 70.8 g in liquid hydrogen at −253° C.), methanol is an excellent carrier of hydrogen fuel. The absence of C—C bonds in methanol, which are more difficult to break, facilitates its transformation to pure hydrogen in 80 to 90% efficiency.

In contrast to a pure hydrogen-based storage system, a reformer system is compact, containing on a volume basis more hydrogen than even liquid hydrogen, and is easy to store and handle without pressurization. A methanol steam reformer is also advantageous in allowing operation at a much lower temperature (250-350° C.) and for being better adapted to on-board applications. Furthermore, methanol contains no sulfur, a contaminant for fuel cells, and no nitrogen oxides are formed from a methanol reformer because of the low operating temperature. Particulate matter and $NO_x$ emissions are virtually eliminated, and other emissions are minimal. Moreover, methanol allows refueling to be as quick and easy as with gasoline or diesel fuel. Thus, an on-board methanol reformer enables rapid and efficient delivery of hydrogen from liquid fuel that can be easily distributed and stored in the vehicle. To date, methanol is the only liquid fuel that has been demonstrated on a practical scale as suitable liquid fuel for a reformer to produce hydrogen for use in a fuel cells for transportation applications.

In addition to on-board reforming, methanol also enables convenient production of hydrogen in fueling stations for refueling hydrogen fuel cell vehicles. A fuel cell, an electrochemical device that converts free chemical energy of fuel directly into electrical energy, provides a highly efficient way of producing electricity via catalytic electrochemical oxidation. For example, hydrogen and oxygen (air) are combined in an electrochemical cell-like device to produce water and electricity. The process is clean, with water being the only byproduct. However, because hydrogen itself must first be produced in an energy-consuming process, by electrolysis or from a hydrocarbon source (fossil fuel) with a reformer, hydrogen fuel cells are still necessarily limited in their utility.

A system for producing high purity hydrogen has been developed by steam reforming of methanol with a highly active catalyst, which allows operation at a relatively low temperature (240-290° C.) and enables flexibility in operation as well as rapid start-up and stop. These methanol-to-hydrogen (MTH) units, ranging in production capacity from 50 to 4000 m³ $H_2$ per hour, are already used in various industries, including the electronic, glass, ceramic, and food processing industries, and provide excellent reliability, prolonged life span, and minimal maintenance. As described above, operating at a relatively low temperature, the MTH process has a clear advantage over reforming of natural gas and other hydrocarbons which must be conducted at above 600° C., because less energy is needed to heat methanol to the appropriate reaction temperature.

The usefulness of methanol has led to development of other reforming processes, for example, a process known as oxidative steam reforming, which combines steam reforming, partial oxidation of methanol, using novel catalyst systems. Oxidative steam reforming produces high purity hydrogen with zero or trace amounts of CO, at high methanol conversion and temperatures as low as 230° C. It has the advantage of being, contrary to steam reforming, an exothermic reaction, therefore minimizing energy consumption. There is also autothermal reforming of methanol, which combines steam reforming and partial oxidation of methanol in a specific ratio and addresses any drawback of an exothermic reaction by producing only enough energy to sustain itself. Autothermal reforming is neither exothermic nor endothermic, and does not require any external heating once the reaction temperature is reached. Despite the aforementioned possibilities, hydrogen fuel cells must use highly volatile and flammable hydrogen or reformer systems.

Regardless, our direct methanol fuel cell (DMFC) that we have invented together with Caltech's JPL utilizing methanol has significant advantages over reformer based fuel cells.

U.S. Pat. No. 5,599,638, of which we are coinventors, discloses a simple direct methanol fuel cell (DMFC) to address the disadvantages of hydrogen fuel cells. In contrast to a hydrogen fuel cell, the DMFC is not dependent on generation of hydrogen by processes such as electrolysis of water or reformation of natural gas or hydrocarbons. The DMFC is also more cost effective because methanol, as a liquid fuel, does not require cooling at ambient temperatures or costly high pressure infrastructure and can be used with existing storage and dispensing units, unlike hydrogen fuel, whose storage and distribution requires new infrastructure. Further, methanol has a relatively high theoretical volumetric energy density compared to other systems such as conventional batteries and the $H_2$-PEM fuel cell. This is of great importance for small portable applications (cellular phones, laptop computers, etc.), for which small size and weight of energy unit is desired.

DMFC offers numerous benefits in various areas, including the transportation sector. By eliminating the need for a methanol steam reformer, DMFC significantly reduces the cost, complexity and weight of the vehicle, and improves fuel economy. A DMFC system is also comparable in its simplicity to a direct hydrogen fuel cell, without the cumbersome problems of on-board hydrogen storage or hydrogen producing reformers. Because only water and $CO_2$ are emitted, emissions of other pollutants (e.g., $NO_x$, PM, $SO_2$, etc.) are eliminated. Direct methanol fuel cell vehicles are expected to be low emission vehicles (ZEV), and use of methanol fuel cell vehicles offers to greatly eliminate air pollutants from vehicles in the long term. Further, unlike ICE vehicles, the emission profile is expected to remain nearly unchanged over time. New fuel cell membranes based on hydrocarbon or hydrofluorocarbon materials with reduced cost and crossover characteristics have been developed that allow room temperature efficiency of ~34%.

Methanol and DME as indicated provide a number of important advantages as transportation fuels. Contrary to hydrogen, methanol storage does not require any energy intensive procedures for pressurization or liquefaction. Because it is a liquid at room temperature, it can be easily handled, stored, distributed and carried in vehicles. It can act as an ideal hydrogen carrier for fuel cell vehicles through on-board methanol reformers or can be used directly in DMFC vehicles. DME although gaseous at room temperature can be easily stored under modest pressure and used effective in admixture with diesel fuels and CNG, or used in residential gas mixtures.

Methanol is also an attractive liquid fuel for static applications. For example, methanol can be used directly as fuel in gas turbines to generate electric power. Gas turbines typically use natural gas or light petroleum distillate fractions as fuel. Compared to such fuels, methanol can achieve higher power output and lower $NO_x$ emissions because of its lower flame temperature. Since methanol does not contain sulfur, $SO_2$ emissions are also eliminated. Operation on methanol offers the same flexibility as on natural gas and distillate fuels, and can be performed with existing turbines, originally designed for natural gas or other fossil fuels, after relatively easy modification. Methanol is also an attractive fuel since fuel-grade methanol, with lower production cost than higher purity chemical-grade methanol, can be used in turbines. Because the size and weight of a fuel cell is of less importance in static applications than mobile applications, various fuel cells other than PEM fuel cells and DMFC, such as phosphoric acid, molten carbonate and solid oxide fuel cells (PAFC, MCFC, and SOFC, respectively), can also be used.

In addition to use as fuels, methanol, DME and derived chemicals have also significant applications in the chemical industry. Today, methanol is one of the most important feedstock in the chemical industry. Most of the some 35 million tons of the annually produced methanol is used to manufacture a large variety of chemical products and materials, including basic chemicals such as formaldehyde, acetic acid, MTBE (although it is increasingly phased out for environmental reasons), as well as various polymers, paints, adhesives, construction materials, and others. Worldwide, methanol is used to produce formaldehyde (38%), methyl-tert-butyl ether (MTBE, 20%) and acetic acid (11%). Methanol is also a feedstock for chloromethanes, methylamines, methyl methacrylate, and dimethyl terephthalate, among others. These chemical intermediates are then processed to manufacture products such as paints, resins, adhesives, antifreeze, and plastics. Formaldehyde, produced in large quantities from methanol, is mainly used to prepare phenol-, urea- and melamine-formaldehyde and polyacetal resins as well as butanediol and methylene bis(4-phenyl isocyanate) MDI foam, which is used as insulation in refrigerators, doors, and in car dashboards and bumpers. Formaldehyde resins are predominantly used as adhesives in a wide variety of applications, e.g., manufacture of particle boards, plywood and other wood panels. Examples of major methanol-derived chemical products and materials produced are shown in FIG. 1.

In producing basic chemicals, raw material feedstocks constitute typically up to 60-70% of the manufacturing costs. The cost of feedstock therefore plays a significant economic role and its continued availability is essential. Because of its economic and long range availability advantages methanol is considered a potential prime feedstock for processes currently utilizing more expensive feedstocks such as ethylene and propylene, to produce chemicals including acetic acid, acetaldehyde, ethanol, ethylene glycol, styrene, and ethylbenzene, and various synthetic hydrocarbon products. For example, direct conversion of methanol to ethanol can be achieved using a rhodium-based catalyst, which has been found to promote the reductive carbonylation of methanol to acetaldehyde with selectivity close to 90%, and a ruthenium catalyst, which further reduces acetaldehyde to ethanol. Another feasible way to produce ethanol from methanol involves conversion of ethylene follow by hydration, the overall reaction being 2CH$_3$→OH C$_2$H$_5$OH+H$_2$O. Producing ethylene glycol via methanol oxidative coupling instead of using ethylene as feedstock is also pursued, and significant advances for synthesizing ethylene glycol from dimethyl ether, obtained by methanol dehydration, have also been made.

Conversion of methanol to olefins such as ethylene and propylene, also known as methanol to olefin (MTO) technology, is particularly promising considering the high demand for olefins, especially in polyolefin and synthetic hydrocarbon products production. The MTO technology is presently a two-step process, in which natural gas is converted to methanol via syn-gas and methanol is then transformed to olefin. It is considered that in the process, methanol is first dehydrated to dimethyl ether (DME), which then reacts to form ethylene and/or propylene. Small amounts of butenes, higher olefins, alkanes, and aromatics are also formed.

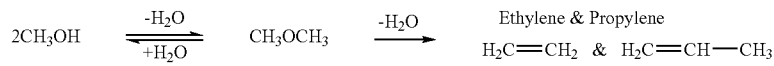

Various catalysts, e.g., synthetic aluminosilicate zeolite catalysts, such as ZSM-5 (a zeolite developed by Mobil), silicoaluminophosphate (SAPO) molecular sieves such as SAPO-34 and SAPO-17 (UOP), as well as bi-functional supported acid-base catalysts such as tungsten oxide over alumina WO$_3$/Al$_2$O$_3$ (Olah), have been found to be active in converting methanol to ethylene and propylene at a temperature between 250 and 400° C. The nature and amount of the end product depend on the type of the catalyst, contact time and other factors of the MTO process used. Depending on the operating conditions, the weight ratio of propylene to ethylene can be modified between about 0.77 and 1.33, allowing considerable flexibility. For example, when using SAPO-34 catalyst according to an MTO process developed by UOP and Norsk Hydro, methanol is converted to ethylene and propylene at more than 80% selectivity, and also to butene, a valuable starting material for a number of products, at about 10%. When using an MTO process developed by Lurgi with ZSM-5 catalysts, mostly propylene is produced at yields above 70%. A process developed by ExxonMobil, with ZSM-5 catalyst, produces hydrocarbons in the gasoline and/or distillate range at selectivity greater than 95%.

There is also a methanol to gasoline (MTG) process, in which medium-pore zeolites with considerable acidity, e.g., ZSM-5, are used as catalysts. In this process, methanol is first dehydrated to an equilibrium mixture of dimethyl ether, methanol and water over a catalyst, and this mixture is then converted to light olefins, primarily ethylene and propylene. The light olefins can undergo further transformations to higher olefins, C$_3$-C$_6$ alkanes, and C$_6$-C$_{10}$ aromatics such as toluene, xylenes, and trimethylbenzene.

With decreasing oil and natural gas reserves, it is inevitable that synthetic hydrocarbons would play a major role. Thus, methanol-based synthetic hydrocarbons and chemicals available through MTG and MTO processes are assuming increasing importance in replacing oil and gas-based materials. The listed uses of methanol in FIG. 1 is only illustrative and not limiting.

Methanol can also be used as a source of single cell proteins. A single cell protein (SCP) refers to a protein produced by a microorganism which degrades hydrocarbon substrates while gaining energy. The protein content depends on the type of microorganism, e.g., bacteria, yeast, mold, etc. The SCP has many uses, including uses as food and animal feed.

Considering the numerous uses of methanol and DME, it is clearly desirable to have improved and efficient methods for their production. Currently, methanol is almost exclusively made from synthesis gas obtained from incomplete combustion (or catalytic reforming) of fossil fuel, mainly natural gas (methane) and coal.

Methanol can also be made from renewable biomass, but such methanol production also involves syn-gas and may not be energetically favorable and limited in terms of scale. As used herein, the term "biomass" includes any type of plant or animal material, i.e., materials produced by a life form, including wood and wood wastes, agricultural crops and their waste byproducts, municipal solid waste, animal waste, aquatic plants, and algae. The method of transforming biomass to methanol is similar to the method of producing methanol from coal, and requires gasification of biomass to syn-gas, followed by methanol synthesis by the same processes used with fossil fuel. Use of biomass also presents other disadvantages, such as low energy density and high cost of collecting and transporting bulky biomass. Although recent improvements involving the use of "biocrude," black liquid obtained from fast pyrolysis of biomass, is somewhat promising, more development is needed for commercial application of biocrude.

The presently existing methods of producing methanol involve syn-gas. Syn-gas is a mixture of hydrogen, carbon monoxide and carbon dioxide, and produces methanol over a heterogeneous catalyst according to the following equations:

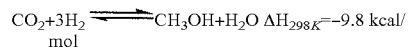

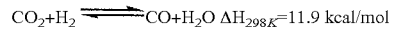

The first two reactions are exothermic with heat of reaction equal to −21.7 kcal.mol$^{-1}$ and −9.8 kcal.mol$^{-1}$, respectively, and result in a decrease in volume. Conversion to methanol is favored by increasing the pressure and decreasing the temperature according to Le Chatelier's principle. The third equation describes the endothermic reverse water gas shift reaction (RWGSR). Carbon monoxide produced in the third reaction can further react with hydrogen to produce methanol. The second reaction is simply the sum of the first and the third reactions. Each of these reactions is reversible, and is therefore limited by thermodynamic equilibrium under the reaction conditions, e.g., temperature, pressure and composition of the syn-gas.

Synthesis gas for methanol production can be obtained by reforming or partial oxidation of any carbonaceous material, such as coal, coke, natural gas, petroleum, heavy oil, and asphalt. The composition of syn-gas is generally characterized by the stoichiometric number S, corresponding to the equation shown below.

$$S = \frac{(\text{moles } H_2 - \text{moles } CO_2)}{(\text{moles } CO + \text{moles } CO_2)}$$

Ideally, S should be equal to or slightly above 2. A value above 2 indicates excess hydrogen, while a value below 2 indicates relative hydrogen deficiency. Reforming of feedstocks having a higher H/C ratio, such as propane, butane or naphthas, leads to S values in the vicinity of 2, ideal for conversion to methanol. When coal is used, however, additional treatment is required to obtain an optimal S value. Synthesis gas from coal requires treatment to avoid formation of undesired byproducts.

The most widely used technology to produce syn-gas for methanol synthesis is steam reforming. In this process, natural gas (of which methane is the major component) is reacted in a highly endothermic reaction with steam over a catalyst, typically based on nickel, at high temperatures (800-1,000° C., 20-30 atm) to form CO and $H_2$. A part of the CO formed react consequently with steam in the water gas shift reaction (WGS) to yield more $H_2$ and also $CO_2$. The gas obtained is thus a mixture of $H_2$, CO and $CO_2$ in various concentrations depending on the reaction conditions: temperature, pressure and $H_2O/CH_4$ ratio

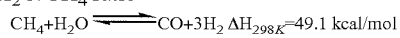

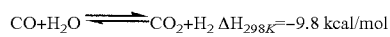

Since the overall methane steam reforming process is highly endothermic, heat must be supplied to the system by burning a part of the natural gas used as the feedstock. The stoichiometric number S obtained by steam reforming of methane is close to 3, much higher than the desired value of 2. This can generally be corrected by addition of $CO_2$ to the steam reformer's exit gas or use of excess hydrogen in some other process such as ammonia synthesis. However, natural gas is still the preferred feedstock for methanol production because it offers high hydrogen content and, additionally, the lowest energy consumption, capital investment and operating costs. Natural gas also contains fewer impurities such as sulfur, halogenated compounds, and metals which may poison the catalysts used in the process.

The existing processes invariably employ extremely active and selective copper-based catalysts, differing only in the reactor design and catalyst arrangement. Because only part of syn-gas is converted to methanol after passing over the catalyst, the remaining syn-gas is recycled after separation of methanol and water. There is also a more recently developed liquid phase process for methanol production, during which syn-gas is bubbled into liquid. Although the existing processes have methanol selectivity greater than 99% and energy efficiency above 70%, crude methanol leaving the reactor still contains water and other impurities, such as dissolved gases (e.g., methane, CO, and $CO_2$), dimethyl ether, methyl formate, acetone, higher alcohols (ethanol, propanol, butanol), and long-chain hydrocarbons. Commercially, methanol is available in three grades of purity: fuel grade, "A" grade, generally used as a solvent, and "AA" or chemical grade. Chemical grade has the highest purity with a methanol content exceeding 99.85% and is the standard generally observed in the industry for methanol production. The syn-gas generation and purification steps are critical in the existing processes, and the end result would largely depend on the nature and purity of the feedstock. To achieve the desired level of purity, methanol produced by the existing processes is usually purified by sufficient distillation. Another major disadvantage of the existing process for producing methanol through syn-gas is the energy requirement of the first highly endothermic steam reforming step. The process is also inefficient because it involves transformation of methane in an oxidative reaction to carbon monoxide (and some $CO_2$), which in turn must be reduced to methanol.

Another way to produce syn-gas from methane is through the partial oxidation reaction with insufficient oxygen, which can be performed with or without a catalyst. This reaction is exothermic and operated at high temperature (1,200 to 1,500° C.). The problem with partial oxidation is that the products, CO and $H_2$ are readily further oxidized to form undesired $CO_2$ and water in highly exothermic reactions leading to S values typically well below 2 and contributing to $CO_2$ induced global warming.

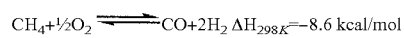

To produce syn-gas without either consuming or producing much heat, modern plants are usually combining exothermic partial oxidation with endothermic steam reforming in order to have an overall thermodynamically neutral reaction while obtaining a syn-gas with a composition suited for methanol synthesis (S close to 2). In this process, called autothermal reforming, heat produced by the exothermic partial oxidation is consumed by the endothermic steam reforming reaction. Partial oxidation and steam reforming can be conducted separately or simultaneously in the same reactor by reacting methane with a mixture of steam and oxygen. The process as mentioned however, produces large amounts of $CO_2$ necessitating its costly sequestering or venting into the atmosphere. Any carbon containing fuel or derived synthetic hydrocarbon product when oxidatively used inevitably forms carbon dioxide and thus is not renewable on the human time scale. There is an essential need to make carbon fuels renewable and thus also environmentally neutral to minimize their harmful effect on global warming.

The selective conversion and recycling of carbon dioxide to methanol without generating unwanted by-products is thus a major challenge and a much desired practical goal. There is a great need to effectively and economically produce methanol from carbon dioxide with high selectivity and yield of conversion. Such is now disclosed in the present invention.

SUMMARY OF THE INVENTION

Our invention relates to a method of preparing methanol and/or dimethyl ether from any source of carbon dioxide (natural or industrially produced) by a novel specific combination of steam and dry reforming of methane or natural gas to give the needed $H_2$ to CO mole ratio of 2 incorporating external carbon dioxide. This method we call the bi-reforming process. It comprises reacting methane under a specific combination of conditions with steam (wet) and $CO_2$ in a specific sequence and mole ratio of reactants sufficient to produce a syn-gas mixture of carbon monoxide/hydrogen ($CO/H_2$) in a ratio of 1:2 and subsequent further conversion of this mixture to methanol and/or dimethyl ether (DME). Advantageously, the bi-reforming mixture can be treated to convert it substantially to methyl alcohol or DME without by-products. Alternatively, unreacted feed components can be readily recovered and recycled.

The needed methane source, depending on its availability, can be natural gas, coal-bed methane, any other natural sources of methane, methane hydrates, as well methane formed by the hydrolysis of aluminium carbide or any other convenient source. The methane source may also contain, besides methane, varying amounts of higher hydrocarbons (ethane, propane, butane, etc.) and/or impurities. It is within the scope of our invention to adjust the amounts of methane, $CO_2$ and $H_2O$ to achieve the reaction conditions of the bi-reforming process.

Our invention represent an efficient new method to convert carbon dioxide with methane (natural gas) to methanol an/or dimethyl ether using a specific gas mixture of two reforming processes i.e steam ($H_2O$) and dry ($CO_2$) reforming to produce a 1:2 molar ratio of CO and $H_2$ (in a process called Bi-reforming™) for the exclusive production of methanol with no production or release of $CO_2$ to the atmosphere or unwanted by-product formation using up costly hydrogen to produce water.

The needed individual processes are:

A. $2CH_4 + 2H_2O \longrightarrow 2CO + 6H_2$ steam reforming
B. $CH_4 + CO_2 \longrightarrow 2CO + 2H_2$ dry reforming
C. $3CH_4 + 2H_2O + CO_2 \longrightarrow 4CO + 8H_2$ overall bi-reforming
$4CH_3OH$ The process can be practiced by carrying out steps A and B separately. The products of reforming of steps A and B are mixed before being introduced into the methanol producing C step. The two reforming steps, however, can also be combined into a single one. In any of the embodiments, no carbon dioxide is produced to be sequestered or released into the atmosphere. Further the complete utilization of $CH_4$ (natural gas) to methanol without producing any by-product represents a significant economical and environmental advantages. This is in contrast to the tri-reforming process of methane in which a synergetic combination of dry reforming, steam reforming and partial oxidation or methane is carried out in a single step, but produces by-products ($CO_2$ and $H_2O$) in the oxidation step representing a significant economic disadvantage and environmental problem. Our present invention using the disclosed bi-reforming approach allows well controlled, high selectivity and yield conversions of carbon dioxide to methanol without any by-product and the difficulties and disadvantages connected using concurrent partial oxidation resulting in undesirable excess carbon dioxide and water. As steam used in the bi-reforming process is readily internally recycled the invention also is adaptable for the production of dimethyl ether from $CO_2$ and methane with no by-product ($H_2O$ or $CO_2$) formation in the overall process which can be represented as $3CH_4 + CO_2 \rightarrow 2CH_3OCH_3$ The aforementioned bi-reforming process thus can also be advantageously used for the preparation of dimethyl ether (DME) without by-product water formation, as is the case in the presently used dehydration of methanol. Until now known reaction of $CO_2$ with methane (dry reforming) was not itself suitable to produce dimethyl ether, as it gives only a 1:1 molar mixture of CO and $H_2$ $CH_4 + CO_2 \rightarrow 2CO + 2H_2$ What enables the now discovered new way to convert methane and $CO_2$ to dimethyl ether is the use of bi-reforming with recycling of formed water into the bi-reforming step, preferentially by way a suitable solid acid catalysts such as Nafion-H.

$3CH_4 + 2H_2O + CO_2 \longrightarrow 4CO + 8H_2$
$4CH_3OH \longrightarrow 2CH_3OCH_3 + 2H_2O$ The DME forming process of $CO_2$ methane thus gives exclusively DME.

$3CH_4 + CO_2 \rightarrow 2CH_3OCH_3$

The aforementioned bi-reforming of $CO_2$ with methane can also be directly applied to natural gas itself to produce methanol and/or DME according to $3C_nH_{(2n+2)} + (3n-1)H_2O + CO_2 \rightarrow (3n+1)CO + (6n+2)H_2 \rightarrow 4nCH_3OH$ effected by either in separate steps or in a single step with proper selection of mixing to obtain the needed 1:2 $CO:H_2$ molar mixture.

A preferred newly discovered catalyst, which is part of our invention for the $CO_2$ bi-reforming process step is $V_2O_5$ and NiO deposited on suitable high surface are a silica carrier, such as nano-structured fused silica i.e. $SiO_2(V_2O_5)NiO$ operating preferably at 800-950° C. Separate steam reforming step is typically performed using nickel catalysts at temperatures of 800-1000° C. according to $CH_4 + H_2O \rightarrow CO + 3H_2$ or $C_nH_m + H_2O \rightarrow nCO + (n+m/2)H_2$ Methanol or dimethyl ether produced via the disclosed bi-reforming process can find utility in numerous applications, either alone, or upon subsequent conversion to other products. Without being limiting, methanol DME and their derived products can be used as synthetic ICE fuels, effective diesel fuels (including mixing varied amounts of DME dimethyl ether with conventional diesel fuel), gasoline-methanol mixed fuels (prepared by adding methanol to gasoline with the fuel having a minimum gasoline content of at least 15% by volume). Without being limited as to other uses, methanol and/or dimethyl ether are convenient energy storage and transportation materials in order to minimize or eliminate the disadvantages or dangers inherent in the use and transportation of LNG or LPG. DME is also a convenient household gas to replace natural gas. They are also convenient raw materials for producing olefins (ethylene, propylene etc.) synthetic hydrocarbons, their products and materials, even for preparing single cell proteins for human or animal consumption.

BRIEF DESCRIPTION OF THE DRAWINGS

The features and benefits of the invention will become more evident from review of the following detailed description of illustrative embodiments and the accompanying drawings.

DESCRIPTION OF THE PREFERRED EMBODIMENTS

Figure 1:
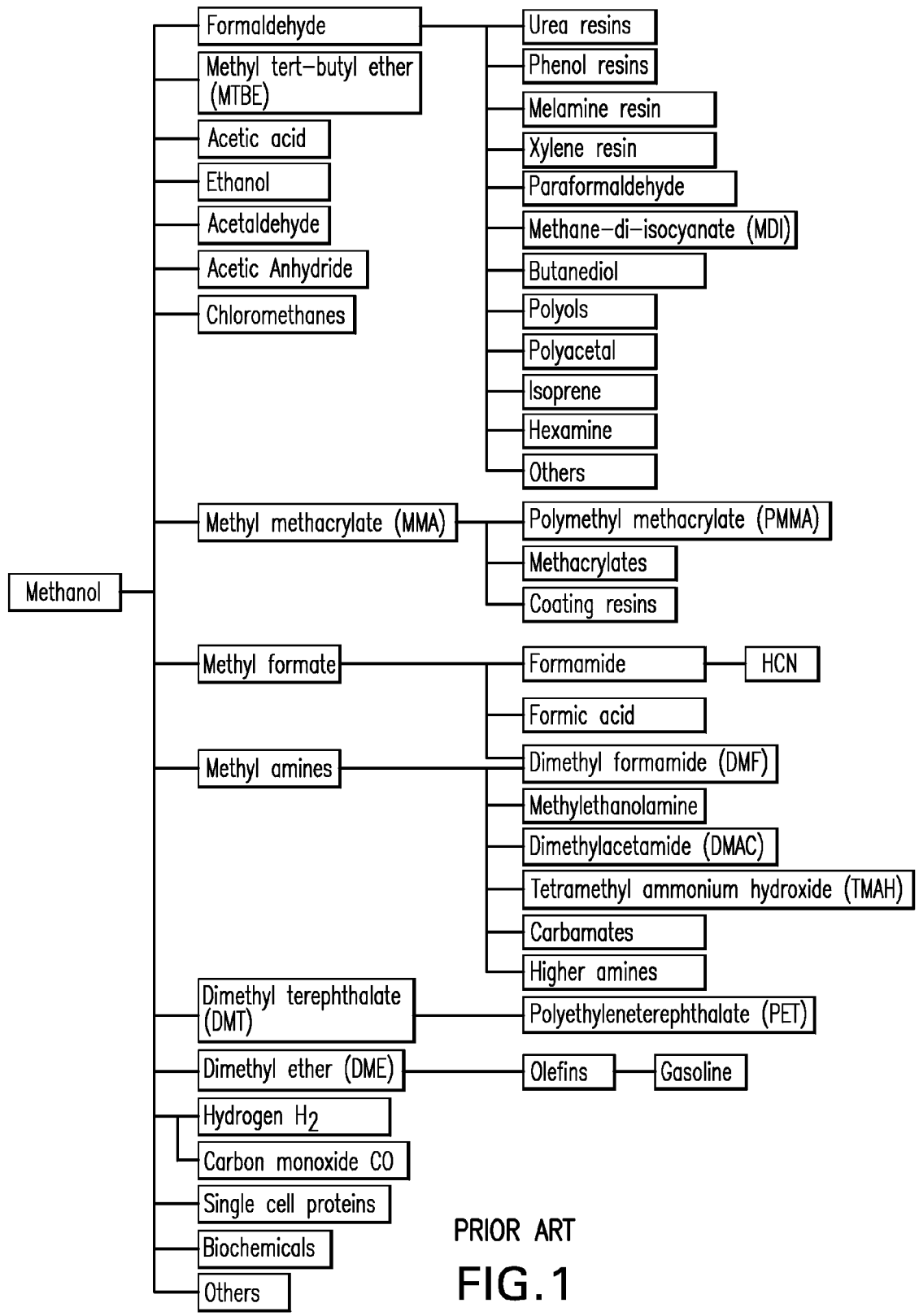
FIG. 1 shows illustrative examples of methanol-derived chemical products and materials.
Figure 2:
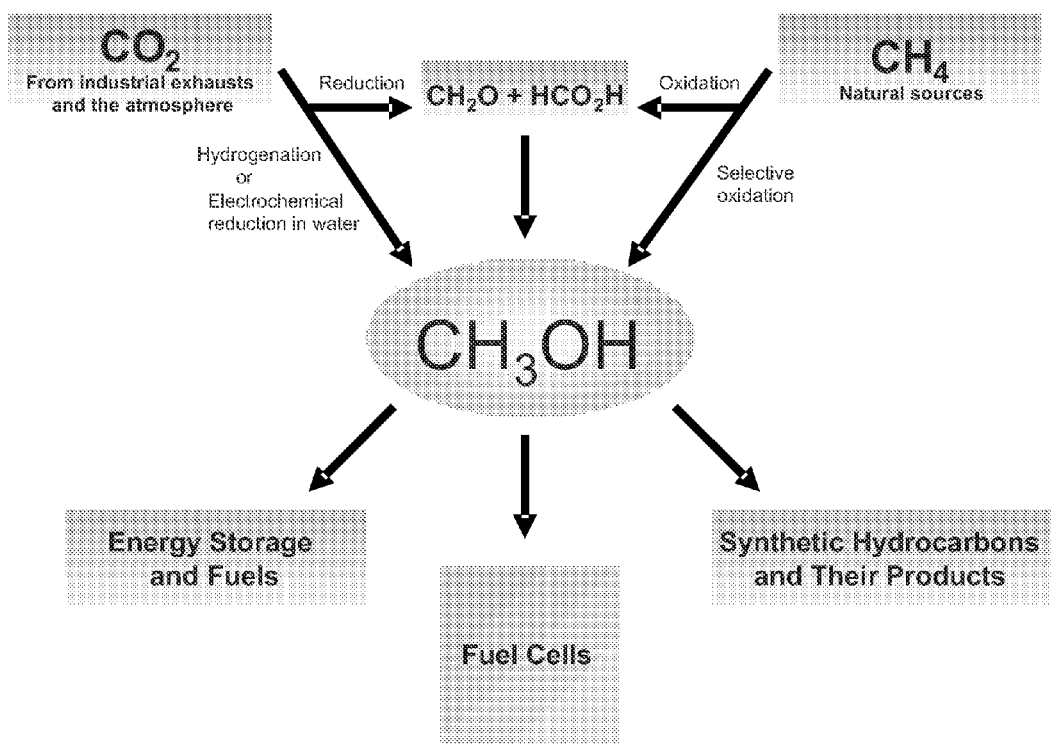
FIG. 2 schematically illustrates the general concept of the inventive process termed the Methanol Economy process by inventor George Olah.

The invention relates to a new, efficient process of conversion of any carbon dioxide source, a methane source such as natural gas, coalbed methane, methane hydrate or any other sources to methanol and/or dimethyl ether with any hydrogen consuming by-products. This new process called bi-reforming is a specific combination of steam ($H_2O$) and dry ($CO_2$) reforming of methane, practiced in two steps or combined into a single step. The method comprises reacting methane or natural gas under a combination of conditions of steam (wet) and dry ($CO_2$) reforming in a specific mole ratio of reactants sufficient to produce mixture of carbon monoxide/hydrogen (CO/$H_2$) in a molar ratio of (1:2), and subsequently further sufficient to convert such mixture of CO and $H_2$ exclusively to methanol and/or dimethyl ether. Advantageously, the mixture of reactants is treated without separation of its components to convert substantially all the reactants to methyl alcohol or dimethyl ether without any by-products. Any unreacted starting or intermediate products can be readily recovered and recycled. The process produces in high selectivity and yield of methanol or dimethyl ether.

As discussed in preceding sections, syn-gas of varying composition can be produced by a variety of reactions. It is generally produced by the reaction of coal or methane natural gas with steam (steam reforming). Syn-gas can also be produced by the reaction of $CO_2$ with methane or natural gas in a process called "$CO_2$" or "dry" reforming, because it does not involve steam.

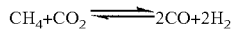

$$CH_4 + CO_2 \rightleftharpoons 2CO + 2H_2$$

The gas mixture produced from methane and $CO_2$, however, has an $H_2$/CO ratio of 1. Therefore, for methanol production, hydrogen generated from other sources must be added to the obtain the needed ratio of 2.

The present invention using bi-reforming of $CO_2$ overcomes this difficulty and produces a $H_2$/CO mixture with a molar ratio of 2, needed for methanol synthesis. It achieves the goal by using a specific combination of steam and dry reforming of methane. In the subsequent methanol synthesis step, substantially all of the hydrogen is converted to methanol. As described in our co-pending patent applications, this subsequent step can be performed, without limitation, by direct catalytic conversion, or by a reaction which involves a methyl formate intermediate.

Steam reforming  $2CH_4 + 2H_2O \longrightarrow 2CO + 6H_2$
Dry reforming  $CH_4 + CO_2 \longrightarrow 2CO + 2H_2$
---
Bi-reforming  $3CH_4 + 2H_2O + CO_2 \longrightarrow$
 $4CO + 8H_2 \longrightarrow 4CH_3OH$ A preferred embodiment of this invention describes the use of a specific combination of steam and dry reforming with a molar ratio of CO:$H_2$ of 1:2 using mixed metal-metal oxide catalysts. The temperature range for the process is in the range of 800 to 1100° C., preferentially at 850-950° C. The newly discovered and developed catalysts for this process show good stability and catalytic activity. Without being limiting, such combinations of catalysts include mixed metal oxides such as NiO—$V_2O_5$, metal-metal oxides such as Ni—$V_2O_5$, ($Ni_2O_3$—$V_2O_5$), as well as mixed oxides such as $Ni_2V_2O_7$ and $Ni_3V_2O_8$, on suitable high surface areas supports such as silica, alumina, metal oxide or metal. One of skill in the art would immediately appreciate that a number of other related metal such as single or mixed catalysts based on V, Ti, Ga, Mg, Cu, Mo, Bi, Fe, Mn, Co, Nb, Zr, La or Sn, and metal oxide catalysts, and their combinations, can achieve the process of the current invention. Suitable reactors for this process can similarly be immediately appreciated by a person of skill in the art. Without being limiting, for example suitable continuous flow reactors can be used to carry out the bi-reforming process in the indicated temperature range.

The BI-REFORMING™ process of the present invention allows for substantially complete utilization and incorporation of all $H_2$ produced into methanol or dimethyl ether. This represents an efficient and economical new way of methanol and/or dimethyl ether production, as well as an efficient new process for recycling of carbon dioxide into methanol (and/or in a subsequent step dimethyl ether), thus rendering the carbon fuels renewable and environmentally carbon neutral. The process is not accompanied by any significant coke formation, as presence of steam in the systems retards coke formation and any carbon deposit still formed is in situ converted by reacting with $CO_2$ to form CO.

As indicated a significant further embodiment of our invention is in the use of bi-reforming in preparing dimethyl ether (DME) using dehydration of produced methanol.

$$3CH_4 + 2H_2O + CO_2 \rightarrow 4CH_3OH \rightarrow 2CH_3OCH_3 + 2H_2O$$

Recycling the equivalent amount of water produced makes the production of DME from methane and $CO_2$ overall $$3CH_4 + CO_2 \rightarrow 2CH_3OCH_3$$

with no external water needed or water produced consuming hydrogen. This is of substantial advantage not only economically but particularly in arid areas when clean, salt free water is not readily available. It is contrasted with the presently used process of the oxidative conversion of methane to DME, where, however, ⅓ of the methane is used up in producing by-product water.

$$2CH_4 + O_2 \rightarrow CHOCH_3 + H_2O$$

Steam and dry reforming are known in the art as separate technologies. Steam reforming of methane to a mixture of CO and $3H_2$ is an extensively used and practiced process (endothermic by 49.1 kcal/mol). Dry reforming of methane to 2CO+ $2H_2$ (endothermic by 59.1 kcal/mol), however, is a relatively less developed process. Our discovered nanostructured silica supported mixed acid catalysts make the $CO_2$ reforming step, however, practical and economical.

As can be appreciated by one of skill in the art, the energy required for the bi-reforming process can come from any suitable energy source, including, but not limited to, excess energy fossil burning power plants produce in off peak use periods, any alternative energy sources, atomic energy, etc. The bi-reforming process of methane or natural gas and carbon dioxide to produce regular dimethyl ether is an energy storage and fuel producing process, but not one of energy production.

In any embodiment, without being limiting, any methane source may be used including natural gas, coalbed gas, a methane hydrate, or the hydrolysis of aluminium carbide. The methane source may contain, besides methane, varying amounts of higher hydrocarbons (ethane, propane, butane, etc.) and/or impurities. Regardless, it is within the scope of the present invention to adjust the amounts of the alkane, $CO_2$ and $H_2$ to achieve the reaction conditions of the BI-REFORMING™ process.

In a further embodiment of the present invention, natural gas containing higher hydrocarbons in various concentrations, can be used for the bi-reforming process according to the following adjustment of the reactants:

$$3C_nH_{(2n+2)} + (3n-1)H_2O + CO_2 \rightarrow (3n+1)CO + (6n+2)H_2$$

(when n=1 represents methane itself)

Any suitable source of natural gas or methane can be used for methanol or DME production according to the present invention. Other than the conventional natural gas sources, they can be produced, for instance, from "biogas," a result of anaerobic bacteria's breaking down organic material in the absence of oxygen. Biogas is produced in the digestive tracks of most mammals, organisms such as termites, and microorganisms during digestion, as well as in wetlands, swamps and bogs, where large amounts of rotting vegetation accumulate. Biogas is composed mainly of methane and carbon dioxide in varying proportions, and contains trace levels of other elements such as hydrogen sulfide ($H_2S$), hydrogen, and/or carbon monoxide.

In all these embodiments, carbon dioxide obtained from any available source, such as, without being limiting, emissions of power plants burning fossil fuels, fermentation processes, calcination of limestone, other industrial sources, or even the atmosphere is utilized via its chemical recycling providing renewable carbon fuels into mitigating the environmentally harmful effect of excess $CO_2$. In a preferred embodiment of the invention, the carbon dioxide source is an exhaust stream from fossil fuel burning power or industrial plant, or a source accompanying natural gas. A non-limiting utility of the present invention is the chemical recycling of carbon dioxide, instead of its sequestration, produced by coal and other fossil fuel burning power plants and industries producing large amounts of carbon dioxide.

In an alternative embodiment of the invention, the carbon dioxide source is the atmosphere. If carbon dioxide content can be separated and absorbed by using various processes as described in the co-pending patent application, (publication no. 20060235091). As an alternative, it is also possible to utilize and recycle the carbon dioxide content of the atmosphere by different chemical processes, as disclosed and claimed in co-pending patent application, publication no. 20060235088.

In these embodiments, the needed hydrogen may be derived from a variety of sources, including the hydrolysis or cleavage of water In a preferred embodiment, an efficient source for $H_2$ is the process of steam reforming of natural gas, including, without limitation, in combination with the water gas shift reaction.

The disclosed bi-reforming process can find multiple utilities. Without being limiting, the combination of steam and dry reforming can be used for the recycling of $CO_2$ emissions from coal and other fossil fuels burning power plants. It is also advantageous for use and recycling of $CO_2$ from natural gas sources, which typically contain substantial $CO_2$ concentrations. This is additionally practical, as $CO_2$ would, otherwise, have to be removed to allow further processing of the natural gas. Some natural gas sources contain $CO_2$ concentration from 5 to 20%. For example, the natural gas at the Sleipner platform in Norway contains, for example, 9% $CO_2$. There, the $CO_2$ is currently already separated and sequestered beneath the North Sea in a deep saline aquifer. Other $CO_2$ separation and sequestration processes are already being practiced in Algeria and other locations, but sequestration is only a temporary, costly storage process with the danger of catastrophic release of large amounts of $CO_2$ when geological events (such as earthquakes) occur.

Methane hydrates are composed of methane trapped by water in cage like structures called clathrates. Methane hydrate could be processed using a combination with bi-reforming where water in the from of steam is added to react with methane. The transformation to syn-gas and further to methanol or DME might render the exploitation of methane hydrate more economical.

Building on the experience with autothermal reforming, the concept of "thermoneutral tri-reforming" has been introduced. This concept is based on the synergetic combination of dry reforming, steam reforming and partial oxidation of methane in a single step. The exothermic oxidation of methane with oxygen produces the heat needed for the endothermic steam and dry reforming reactions allowing to reach a suitable S value of syngas for methanol production. However, the involved oxidation of methane with oxygen also produces excess of carbon dioxide because of its effect on global warming represents a serious environmental hazard. The disclosed bi-reforming process minimizes this problem.

Methanol or dimethyl ether produced according to our disclosed invention can find utility in numerous applications, either on their own, or with subsequent conversion to other products. Without being limiting, methanol and dimethyl ether can be used as suitable synthetic fuels, replacing our diminishing fossil fuel sources improved diesel fuels, transportation fuels. They are also useful as convenient energy storage and transportation materials, which minimize or eliminate the disadvantages or dangers inherent in the use and transportation of LNG or LPG. They are also of great significance as starting materials for light olefins (ethylene, propylene, etc.) and subsequently to synthetic hydrocarbons and their varied products. It is also possible to use them for preparing single cell proteins for human or animal alimentation.

The invention described and claimed herein is not to be limited in scope by the specific embodiments herein disclosed, as these embodiments are intended as illustrative of several aspects of the invention. Any equivalent embodiments are intended to be within the scope of this invention, as they will become apparent to those skilled in the art from the present description. Such embodiments are also intended to fall within the scope of the appended claims.

EXAMPLE 1

A suitable molar mixture of $CO_2$, methane (or natural gas) and steams is bi-reformed in a flow reactor over $V_2O_5$/NiO catalyst support on silica at a temperature of ~800-850° C. producing a gas mixture with a molecular approximate ratio of CO and $2H_2$ with a conversion of methane and $CO_2$ in excess of 90%.

EXAMPLE 2

Support of catalyst in example 1 is fused silica having a suitably large nanostructural surface.

EXAMPLE 3

Recycling of water formed in the bi-reforming process of Example 1 allows continuous conversion of $CO_2$ with methane (natural gas) exclusively to give dimethy ether.

EXAMPLE 4

Exit streams of Examples 1 and 2 were combined in a ratio to obtain gas mixture of a 2:1 mole ratio of $H_2$ and CO, which is subsequently converted to methanol using usually practical conditions over copper based catalysis.

EXAMPLE 5

A mixture of methane, $CO_2$ and $H_2O$ (3:1:2 mole ratio) were reacted (bi-reformed) over a catalyst composed of $V_2O_5$/NiO supported on nanostructural high surface area fused silica to give a H₂/CO gas mixture of 2:1 suitable for exclusive production of methanol according to Example 4.

EXAMPLE 6

Producing dimethyl ether (DME) by the dehydration of methanol formed according to example 5 using a solid acid catalyst such as Nafion H.

EXAMPLE 7

Producing dimethyl ether (DME) according to Example 6 by recycling water formed into the reaction mixture as in example 5 allowing DME to be formed by just utilizing $CH_4$ and $CO_2$ in a 3:1 overall molar ratio.

What is claimed is:

1. A process of making exclusively dimethyl ether from carbon dioxide and a methane source which comprises:
    preparing methanol from carbon dioxide and a methane source by:
        combining wet reforming and dry reforming of sufficient amounts of methane, carbon dioxide and water under reaction conditions sufficient to produce an essentially 2:1 molar mixture of hydrogen and carbon monoxide; and
        converting the essentially 2:1 hydrogen and carbon monoxide mixture under conditions sufficient to form methanol;
    dehydrating the methanol thus produced; and
    recycling any water that is present under conditions sufficient to utilize only carbon dioxide and methane from the methane source to produce exclusively dimethyl ether.

2. The method of claim 1, wherein the combining of the wet and dry reforming is conducted either in separate two steps or combined in a single step with the methane, carbon dioxide and water present in sufficient stoichiometric amounts to provide the hydrogen and carbon monoxide for production of methanol.

3. The method of claim 2 wherein the methane, carbon dioxide and water present in the single combined bi-reforming step are present in a mole ratio of about 3:1:2 to provide a mixture of hydrogen and carbon monoxide in a mole ratio of about 1:2.

4. The method of claim 1, wherein substantially all of the carbon monoxide and hydrogen are converted to methanol.

5. The method of claim 1, wherein the combined bi-reforming is conducted at a temperature range of about 800 to 1100° C.

6. The method of claim 1, wherein the bi-reforming is conducted in the presence of a combination of a metal and a metal oxide catalysts.

7. The method of claim 6, wherein the catalyst combination is Ni and $V_2O_5$; $Ni_2O_3$ and $V_2O_5$; or $Ni_2V_2O_7$ and $Ni_3V_2O_8$.

8. The method of claim 7, wherein the catalyst combination is supported on a high surface or nanostructured support.

9. The method of claim 8, wherein the support comprises silica, alumina, a metal oxide or a metal.

10. The method of claim 1, wherein the combined wet and dry reforming is conducted in the presence of a combination of metal oxide catalysts.

11. The method of claim 10, wherein the catalyst combination is supported on a high surface or nanostructured support.

12. The method of claim 11, wherein the support comprises silica, alumina, a metal oxide or a metal.

13. The method of claim 1, wherein the combined wet and dry reforming is conducted in the presence of an added catalyst that includes single or mixed catalysts based on V, Ti, Ga, Mg, Cu, Mo, Bi, Fe, Mn, Co, Nb, Zr, La or Sn.

14. The method of claim 13, wherein the catalyst combination is supported on a high surface or nanostructured support.

15. The method of claim 14, wherein the support comprises silica, alumina, a metal oxide or a metal.

16. The method of claim 1, wherein the methane source is natural gas, coal bed methane, methane hydrates, or aluminum carbide based methane.

* * * * *

UNITED STATES PATENT AND TRADEMARK OFFICE
CERTIFICATE OF CORRECTION

PATENT NO.      : 7,906,559 B2
APPLICATION NO. : 11/850501
DATED           : March 15, 2011
INVENTOR(S)     : Olah et al.

Page 1 of 1

It is certified that error appears in the above-identified patent and that said Letters Patent is hereby corrected as shown below:

Title Page:
Item (57) ABSTRACT, lines 7-8, change "BI-REFORMING™" to -- bi-reforming --

Column 11:
Line 9, change "Bi-reforming™)" to -- bi-reforming) --

Column 14:
Line 3, change "BI-REFORMING™" to -- bi-reforming --
Lines 57-58, change "BI-REFORMING™" to -- bi-reforming --

Signed and Sealed this
Twenty-sixth Day of April, 2011

David J. Kappos
*Director of the United States Patent and Trademark Office*